United States Patent [19]

Tyler et al.

[11] Patent Number: 5,118,898
[45] Date of Patent: Jun. 2, 1992

[54] PROCESS FOR THE PRODUCTION OF OLEFINS BY COMBINED METHANE OXIDATIVE COUPLING/HYDROCARBON PYROLYSIS

[75] Inventors: Ralph J. Tyler, Elanora Heights; James H. Edwards, East Ryde; Peter J. Jackson, Ferny Creek, all of Australia

[73] Assignees: The Broken Hill Proprietary Company Limited, Melbourne; Commonwealth Scientific & Industrial Research Organization, Campbell ACT, both of Australia

[21] Appl. No.: 493,729

[22] Filed: Mar. 14, 1990

[30] Foreign Application Priority Data

Jun. 30, 1989 [AU] Australia .................. PJ5021

[51] Int. Cl.$^5$ ........................... C07C 2/00; C07C 5/00
[52] U.S. Cl. ........................... 585/500; 585/943
[58] Field of Search ........................... 585/500, 943

[56] References Cited

FOREIGN PATENT DOCUMENTS 0336823 10/1989 European Pat. Off. .

Primary Examiner—H. M. S. Sneed
Assistant Examiner—James Saba
Attorney, Agent, or Firm—Armstrong, Nikaido, Marmelstein, Kubovcik & Murray

[57] ABSTRACT

A process for the production of ethylene from a methane rich gas stream and an ethane rich gas stream. The process comprises the steps of:

(a) introducing the methane rich gas stream together with molecular oxygen into a lower zone of a fluidized-bed of particles which are catalytically active in promoting an exothermic oxidative coupling reaction to produce ethylene and other hydrocarbons, (b) mixing the ethane rich gas stream into the fluidized-bed above the level at which substantially all of the molecular oxygen has been consumed, and (c) subjecting the mixture resulting from step (b) to an endothermic pyrolysis reaction in an upper zone of the fluidized-bed to produce further ethylene and other olefinically unsaturated hydrocarbons.

The process is characterized in that the pyrolysis step (c) is carried out substantially without the addition of heat to the reactor, other than the heat content of the methane rich and ethane rich gas streams and the heat generated by the exothermic oxidative coupling reaction. The fluidized bed particles are desirably caused to circulate within the reactor in such a manner that there is an efficient transfer of exothermic heat from the oxidative coupling zone to the pyrolysis zone so that the reactions of steps (a) and (c) occur at substantially the same temperature.

9 Claims, 2 Drawing Sheets

PROCESS FOR THE PRODUCTION OF OLEFINS BY COMBINED METHANE OXIDATIVE COUPLING/HYDROCARBON PYROLYSIS

FIELD OF THE INVENTION

The present invention relates to a process which combines the oxidative coupling of methane with the pyrolysis of ethane and/or higher hydrocarbons to produce unsaturated hydrocarbons, principally ethylene, and more particularly to such a process wherein the oxidative coupling and pyrolysis are carried out in a single fluidized-bed reaction system.

BACKGROUND ART

Ethylene is the single most important industrial hydrocarbon chemical and the process of choice for its manufacture is the pyrolysis of ethane and higher hydrocarbons. The pyrolysis reactions involved in ethylene production are highly endothermic and are conventionally carried out at moderate to high temperatures (800°-950° C.) depending on the feedstock used. The pyrolysis is conducted in fired tubular reactors in which the hydrocarbon feed, mixed with steam, is passed through tubes located in a furnace where the heat for pyrolysis is transferred to the feed indirectly through the walls of the tubes. The product stream from the pyrolysis furnace is rapidly quenched to prevent secondary undesired reactions, cooled to recover its heat content and then passed to the product recovery section for separation of the products and byproducts. Any unconverted feed, which in the case of ethane pyrolysis is about 40% of the feed, is separated from the pyrolysis products and recycled to the pyrolysis furnace where it is pyrolysed to extinction. The hydrogen and other fuel byproducts from pyrolysis are generally consumed within the process as fuel for the pyrolysis furnace.

The process suffers from the disadvantage that, due to the high temperatures required for pyrolysis and the need to supply the heat of reaction indirectly from furnace combustion gases, the design of the pyrolysis reactor and furnace is complex and involves very costly materials of construction. The system is further complicated by the need to recover large amounts of energy (usually in the form of steam which is consumed by the process) from the furnace combustion gases in order for the process to be thermally efficient.

A further disadvantage of conventional pyrolysis technology for ethylene production is that methane is excluded from being a feedstock because its decomposition temperature is too high and the yield of useful products too low. Being the major component of natural gas, methane is the most abundant and cheapest hydrocarbon available. Consequently there has been much research into developing methods for the direct conversion of methane into higher valued products. Direct conversion, as used here, signifies any conversion process which does not involve as a first step the production of a synthesis gas (CO and $H_2$) from methane by the processes of steam reforming or partial oxidation.

One such direct methane conversion technique is oxidative coupling which involves reacting methane with oxygen over a suitable catalyst to produce higher hydrocarbons (principally ethane and ethylene) in a single step. There is currently worldwide interest in this route as a methane conversion process and extensive research activity has resulted in a substantial number of publications and patents in this area.

The reaction pathway in methane oxidative coupling has been shown to involve the oxidative extraction of a hydrogen atom from a molecule of methane by the catalyst to form a methyl ($CH_3$) radical followed by the coupling of two $CH_3$ radicals to form the primary product ethane. The desired product ethylene arises from further reactions of ethane which may or may not involve the catalytic surface. Other higher hydrocarbons such as propylene, butadiene etc., are formed in minor amounts. Undesired products such as carbon monoxide and carbon dioxide are also formed together with water and hydrogen.

It is a general characteristic of methane coupling that the selectivity to hydrocarbons (i.e. the methane converted to hydrocarbons expressed as a percentage of the total methane converted) declines as the per pass methane conversion (i.e. the percentage of input methane converted to products per pass) increases. Consequently, in order to maintain a satisfactory selectivity to hydrocarbons, a commercial process based on this route would need to operate at per pass methane conversions considerably lower than 100%. Current research indicates that the per pass methane conversion will be limited to the range 25-50% and this will necessitate the recycling of the unconverted methane back to the reactor after separation of the reaction products and byproducts. The need for recycling large quantities of methane means that oxygen rather than air is preferred for use as an oxidant.

It has been proposed in Australian Patent Application 32442/89 to produce olefins from natural gas containing methane and ethane by a process involving:

(a) separating the natural gas into two fractions, a first methane rich gas fraction and a second ethane rich gas fraction, (b) oxidizing the first gas fraction with molecular oxygen in the presence of a suitable catalyst allowing the oxidative coupling of the methane into superior hydrocarbons, (c) mixing the effluent from stage (b) with the ethane rich gas fraction when at least about 80% by volume of the molecular oxygen has been already consumed in stage (b), and (d) pyrolysing the mixture resulting from stage (c).

This specification describes and exemplifies the use of two separate reactors for the steps (b) and (d) and uses a fixed-bed of catalyst for step (b). Whilst the fixed bed reactor is the preferred mode of operation, the specification indicates that a single reactor vessel could be used and also suggests the use of a catalytic fluidized-bed for the process. The specification of patent application 32442/89 notes that the addition of the ethane to effluent from the oxidative coupling reaction will cause a fall in the mixed gas temperature. This results from the fact that the only heat available for pyrolysis in a fixed-bed reaction system is the sensible heat contained in the effluent gas from the oxidative coupling zone. In view of the temperature requirements of both the oxidative coupling and pyrolysis processes this severely restricts the amount of ethane or higher hydrocarbons that can be pyrolysed without the supply of additional heat.

The present inventors have realized that a further improvement in the process may be obtained if both of the reactions (i.e. oxidative coupling and pyrolysis), are carried out within a fluidised-bed reactor containing suitable catalyst particles under conditions which allow the efficient transfer of the entire heat from the oxidative coupling reaction to the pyrolysis zone, both by the gas and by circulation of the solid particles, in such a manner that the two reactions proceed substantially isothermally and substantially autothermally.

Accordingly, the present invention consists in a process for the production of ethylene and other olefinically unsaturated hydrocarbons from a first methane rich gas stream and a second gas stream rich in ethane and/or other higher hydrocarbons, comprising:

(a) introducing the first gas stream together with molecular oxygen into a lower zone of a fluidised-bed of particles which are catalytically active in promoting the exothermic oxidative coupling reaction of methane to produce ethylene and other hydrocarbons, (b) mixing the second gas stream into the fluidised-bed above the level at which substantially all of the molecular oxygen has been consumed, and (c) subjecting the mixture resulting from step (b) to an endothermic pyrolysis reaction in an upper zone of the fluidised-bed to produce further ethylene and other olefinically unsaturated hydrocarbons, the process is characterized in that the endothermic pyrolysis step (c) is carried out substantially without the addition of heat to the reactor other than the heat content of the first and second gas streams and the heat generated by the exothermic oxidative coupling reaction.

Preferably the operation of the fluidised-bed causes the circulation of the particles in such a manner that there is an efficient transfer of the exothermic heat from the oxidative coupling zone to the pyrolysis zone so that the reactions of steps (a) and (c) occur at substantially the same temperature.

As used in this specification the term "substantially the same temperature" in respect to the carrying out of the oxidative coupling and pyrolysis reactions means that the reactions are carried out at average temperatures within 100° C. of one another and more preferably within 50° C. of one another and most preferably within 20° C. of one another. Each of the two reaction zones preferably are operated at an average temperature of from 770° C. to 930° C.

In view of the favorable characteristics of fluidised-bed reactors described above it is possible to pyrolyse substantially greater proportions of higher hydrocarbons than are contained in natural gas (as specified in Australian patent application 32442/89). Thus in the process according to the present invention the mole ratio of ethane or higher hydrocarbons converted by pyrolysis of the second stream to that of methane converted by oxidative coupling of the first stream is in the range from 0.01:1 to 7:1, and preferably in the range from 0.4:1 to 3:1.

It is a feature of the current invention that methane oxidative coupling is combined with higher hydrocarbon pyrolysis resulting in an improved process for producing ethylene which overcomes many of the disadvantages and limitations of each of the two processes individually and of the previously proposed coupling of these processes. This is achieved by conducting the hydrocarbon pyrolysis and methane coupling reactions within the same reaction system in a manner by which the surplus exothermic heat from methane coupling is utilized to pyrolyse ethane or higher hydrocarbons.

A significant advantage of the process according to the present invention is that the reactor is an autothermal reactor, that is the overall heat requirements for the reaction are generated within the reaction zone thus eliminating the need for indirect heat transfer as required in a conventional pyrolysis reactor. This improves the efficiency of reaction heat utilization, reduces the cost of materials of construction and greatly simplifies process heat recovery since the pyrolysis furnace and its associated flue gas heat recovery system are no longer required.

A further advantage of the process is that the accumulation of carbon on the catalyst in the pyrolysis zone of the reactor can be avoided. In the pyrolysis step elemental carbon is invariably formed to a small extent and this is normally laid down on any catalyst particles present in the pyrolysis zone This quantity of formed carbon, which can be negligible in terms of reactor yield and process efficiency, would ultimately necessitate any fixed-bed catalytic reactor being taken off line for carbon removal and catalyst regeneration. This considerably increases process complexity and costs. In the present process, however, any carbon laid down on the catalyst particles is carried by the particles back into the oxygen containing zone where the carbon is combusted to produce carbon oxides. In this way accumulation of carbon on the catalyst is eliminated and the catalyst can operate indefinitely in a carbon free condition.

It has been found that fluidised-bed reactors are particularly well suited for conducting the methane coupling process from the viewpoint of controlling reaction temperature, due to the excellent backmixing and internal recirculation of the catalyst particles within the fluidised-bed. This feature of fluidised-beds also has advantages in the context of the present invention in that the recirculating catalyst particles also acts as the heat carrying agent for transferring heat from the oxidative coupling zone of the reaction system to the pyrolysis zone. The pyrolysis step can thus be conducted at essentially isothermal conditions and at similar temperatures to that of the methane oxidative coupling process. As previously mentioned, this is a desirable operating condition for both processes. The fluidised-bed reaction mode also has the further advantage that the heat available for pyrolysis is not simply restricted to the sensible heat of the gas passing from the methane oxidative coupling zone to the hydrocarbon pyrolysis zone. Since the majority of the heat transfer in a fluidised-bed is accomplished via the recirculating catalyst particles the operating conditions of the methane oxidative coupling process (i.e. the per pass methane conversion and selectivity to hydrocarbons) can be chosen such that any desired amount of heat can be made available for the hydrocarbon pyrolysis by simple adjustment of the oxygen flow to the oxidative coupling zone of the fluidised-bed. This affords considerable flexibility in the relative amounts of methane and higher hydrocarbons which can be processed in the conversion reactor. This flexibility, due to the capability of the fluidised-bed reaction mode to control both the temperature and the amount of heat available for pyrolysis, is not possible in a fixed-bed reactor where the catalyst particles remain stationary with respect to each other. In a fixed-bed reactor the heat effects associated with the oxidative coupling and pyrolysis processes would lead to unfavorable temperature gradients within the reaction zone and this would severely restrict reactor operation for this combined process.

The catalyst recirculation can be internal with a single fluidised-bed as would be the case for a reactor which is operating in the well known bubbling-bed or turbulent regimes of fluidization. Alternatively the catalyst recirculation can be external, as in the case of the well-known circulating fluid-bed and riser reactor modes, provided the heat transfer characteristics between the two reaction zones, as described above, are maintained.

It has been found that many of the known methane coupling catalysts are extremely active and when these catalysts are operated in a fluidised-bed reactor a total consumption of reactant oxygen is attained in the bottom section of the bed. Under these circumstances the majority of the fluidised-bed is in an oxygen-free environment. The present inventors have also shown that the expected back mixing of the second gas stream into the oxygen containing zone by the circulation of the fluidised bed particles does not occur. These are both particularly favorable situations for the present invention since taken together they allow great flexibility in the location of the injection point for the higher hydrocarbons to maximize their pyrolytic conversion whilst minimizing the possibility of these hydrocarbons entering the oxygen containing zone of the reactor. In this way not only is the pyrolysis step conducted isothermally, and hence under conditions favoring high per pass conversion, but also it would be conducted with a selectivity to desired products approaching 100% whilst at the same time ensuring that the hydrogen produced by pyrolysis is not combusted to water. By contrast if the hydrocarbons were added to the oxygen-containing zone of the reactor they, along with the hydrogen produced by pyrolysis, would at least partly be combusted to carbon oxides and water thus leading to a loss in process efficiency.

The oxidative coupling catalyst may be any suitable one of the wide range of known oxidative coupling catalysts which are referred to in Australian Patent Specification 32,442/89. It is however recognized that in a fluidised-bed the particles are preferably abrasion resistant and for this reason the preferred catalysts are those which can themselves be formed into abrasion resistant particles or which may be incorporated into or coated onto abrasion resistant particles. Particularly preferred catalysts are those described in the present applicants co-pending Australian patent applications PJ5021 nd PJ5806. These most preferred catalysts comprise a clay and a compound of a Group 11A element that is capable under reaction conditions of existing at least partly in its oxide or carbonate form. The compound is most preferably an oxide of a Group 11A element, e.g. strontium oxide. The catalyst preferably also contains a compound of a Group 1A element that is capable under reaction conditions of existing at least partly in its oxide or carbonate form.

Hydrogen is produced as a byproduct both by the methane coupling reaction and hydrocarbon pyrolysis. In the present invention the hydrogen can be recovered from the unconverted methane or, alternatively, a methanation step can be included in which the hydrogen is reacted with byproduct carbon oxides to produce methane which can be recycled to the oxidative coupling zone of the reactor. Inclusion of the methanation step has the potential to improve the overall carbon utilization efficiency of the process.

BRIEF DESCRIPTION OF THE DRAWINGS

Hereinafter given by way of example only is a preferred embodiment of the invention described with reference to the accompanying drawings in which.

BEST METHOD FOR CARRYING OUT THE INVENTION

Figure 1:
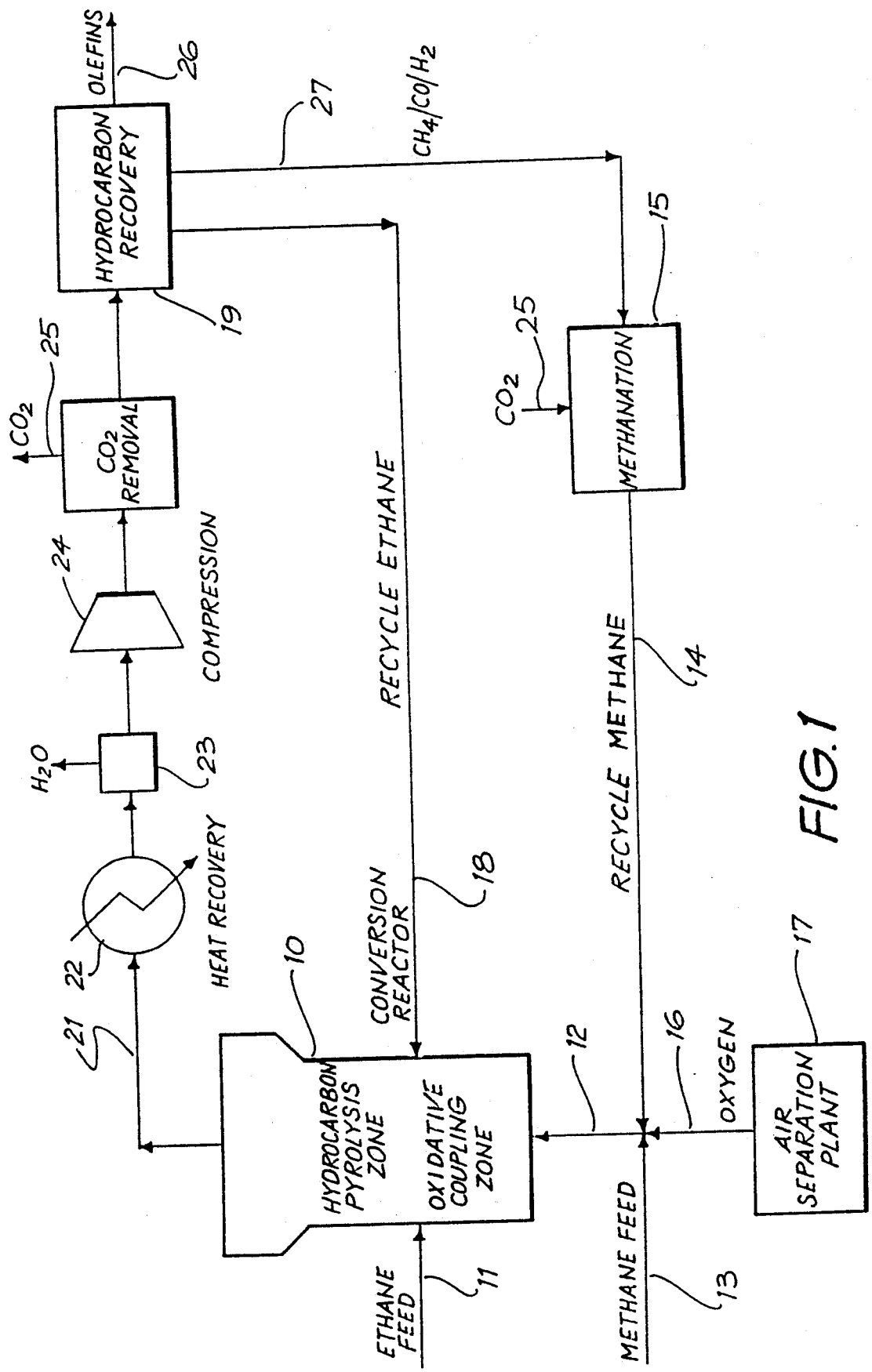
FIG. 1 is a diagrammatic representation of an arrangement for carrying out a conceptual process according to the present invention.

The diagrammatic representation of FIG. 1 is based on a process using a single fluidised-bed reactor 10 and a feedstock consisting of separate streams of ethane 11 and methane 13.

The reactor feed 12, consisting of fresh methane feed 13 and recycle methane 14 from the methanation section 15 of the process, mixed with oxygen 16 produced in an air separation plant 17, is fed to the oxidative coupling section of the reactor 10. Here part of the methane reacts rapidly with all of the oxygen by contacting with the fluidised-bed of catalyst to produce a mixture of $C_2+$ hydrocarbons (principally ethane and ethylene), carbon oxides, hydrogen and water. The products pass through the oxygen-free zone of the fluidised-bed 10 where ethane (consisting of fresh feed 11 and ethane 18 recycled from the hydrocarbon recovery section 19) is injected and partly pyrolysed to ethylene and hydrogen solely using heat which is generated by oxidative coupling and transferred to the pyrolysis zone by the recirculating catalyst particles.

The combined product stream 21 from the conversion reactor 10 is cooled in heat exchanger 22 to recover heat which is used to supply the total energy demand of the overall process. It is a feature of this process that the conversion reactor can be operated at the appropriate conditions of methane conversion and hydrocarbon selectivity such that the amount of energy recoverable from the reactor product gas is equal to that required by the entire process as described with reference to FIG. 1 (i.e. it can be operated in an energy-balanced mode for any particular set of feedstocks).

After cooling, the product gas 21 is dehydrated in dehydrator 23 and compressed in compressor 24 and treated to remove byproduct $CO_2$ 25 and then passed to the hydrocarbon recovery section 19 where the $C_2+$ hydrocarbons are separated (most likely by conventional cryogenic distillation) from the unconverted methane. The unsaturated hydrocarbons are separated from ethane and removed as products 26 whilst the ethane 18 is recycled to the pyrolysis zone of the reactor 10.

The methane recycle stream 27, which also contains CO and $H_2$, passes through the methanation reactor 15 where sufficient of the $CO_2$ 25 removed prior to the hydrocarbon recovery step is added back into this stream such that the hydrogen is completely consumed in converting both CO and $CO_2$ back to methane. The methane 14 formed by methanation is recycled along with the unconverted methane back to the oxidative coupling zone of the conversion reactor 10.

For the case where the process is based on a natural gas feed it is necessary to include a feed gas pretreatment step in which the ethane and higher hydrocarbons are separated from methane prior to the conversion reactor. These non-methane hydrocarbon components can then be fed separately to the pyrolysis zone of the conversion reactor.

EXAMPLE

The following example, based on experimental data obtained in a small fluidised-bed reactor, illustrates that the methane oxidative coupling and hydrocarbon pyrolysis steps can be combined within a single reactor to achieve the benefits claimed in the present invention.

In this example, a gas stream containing 83% v.v/methane and 17% v/v oxygen was fed continuously to a 60 mm dia. fluidized-bed reactor at the rate of 12.3 g-mol $h^{-1}$ The reactor contained 70 g of catalyst and was operated at 850° C. in the bubbling-bed mode. The nominal height of the fluidised-bed was 6 cm. Axial gas samples extracted from the fluidised-bed showed that the oxygen had been completely consumed at 0.3 cm above the feed gas distributors and that the remainder of the bed above this point was in an oxygen-free environment.

Performance measurements under these conditions indicated that the reactor was operating with a per pass methane conversion of 24.8% whilst the selectivity to hydrocarbons was 66.6% (9% to ethane and 57.6% to unsaturated hydrocarbons) and the selectivity to carbon oxides was 33.4% (27.2% to carbon dioxide and 6.2% to carbon monoxide). The methane conversion rate was 2.53 g-mol $h^{-1}$.

With the reactor operating in this manner, ethane was injected directly into the fluidised-bed at the rate of 2.6 g-mol $h^{-1}$ at a point in the oxygen-free zone of the bed some 3 cm above the feed gas distributor plate. Measurements showed that about 65% of the input ethane was converted to unsaturated hydrocarbons, mainly ethylene, and hydrogen.

Upon injection of the ethane a very small increase in the production rate of carbon oxides was observed amounting to about 1% of the ethane pyrolysed. This increase in carbon oxides resulted from the previously discussed mechanism occurring in the fluidised-bed in which carbon formed by ethane cracking is subsequently combusted to carbon oxides in the oxidative coupling zone. A notable feature of the experiments has been that all catalyst including that used in this example after recovery showed no evidence whatsoever of carbon accumulation, demonstrating that the reactor can be operated indefinitely without the need for a carbon removal step. Yield measurements showed that the pyrolysis of the ethane was being conducted within the fluidised-bed with a selectivity to ethylene and other unsaturated hydrocarbons in excess of 95%. This demonstrates the essential feature of the present invention namely that the oxidative coupling of methane and hydrocarbon pyrolysis processes can be conducted efficiently within a fluidised-bed reactor with the heat of pyrolysis being supplied in situ via the recirculating catalyst particles without the use of supplementary heating of the pyrolysis zone of the reactor.

Figure 2:
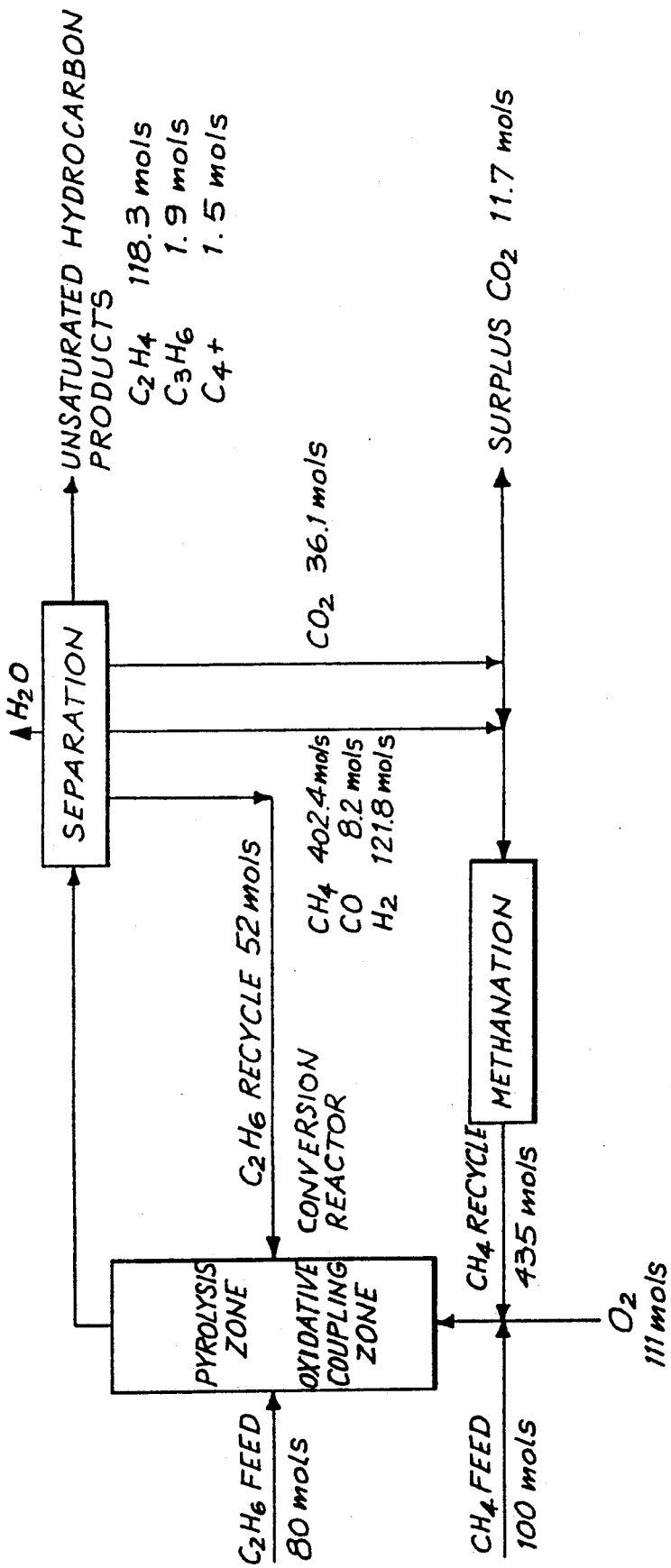
FIG. 2 is a diagrammatic representation of a mass balance simulation of a process according to the present invention.

An ideal process mass balance simulation has been prepared based on the above experimental results for methane oxidative coupling and ethane pyrolysis, and it is shown in the accompanying diagram (FIG. 2). This simulation also includes a methanation step in the methane recycle system for the utilization of hydrogen produced by methane coupling and ethane pyrolysis.

The results in FIG. 2 show that if the process is now considered as one in which carbon in methane and eth- ane is converted to desired products (unsaturated hydrocarbons) and undesired byproduct carbon dioxide, the combined coupling/pyrolysis process produces unsaturates at an overall selectivity greater than 95%. The per pass conversions of ethane and methane are 65 and 24.8% respectively, resulting in an overall per pass carbon conversion of 36.6%. About 64% of the product hydrocarbons are derived from ethane and 36% from methane.

The benefit of including the methanation step can be illustrated by the fact that, if it was not included in FIG. 2, none of the carbon oxides produced from methane coupling would be converted back to methane and this would result in the selectivity to unsaturates being reduced to less than 85%.

COMPARATIVE ANALYSIS

(a) Australian Patent Application 32442/89

In example number 4 (Table 1) of the Australian patent application 32442/89 the oxidative coupling zone of the small-scale experimental fixed-bed reactor is maintained at 880° C. whilst the gas phase pyrolysis zone after this reactor is maintained at 850° C. The data in Table 1 of Australian Patent Application 32.442/89 shows that 0.368 mol of added $C_2H_6$ are converted in the pyrolysis zone per mol of $CH_4$ converted in the oxidative coupling zone. Heat balance calculations have been conducted with varying degrees of preheating of the added ethane prior to pyrolysis to determine if it is possible to operate a reactor adiabatically and achieve the degree of ethane conversion specified in Example 4. The maximum amount of external preheating of the ethane which could be achieved in practice would be around 600° C. in order to prevent the onset of pyrolysis in the ethane preheater.

The results of the heat balance calculations are shown in Table 1 of this specification. In all cases the final calculated temperature in the pyrolysis zone is far too low from the viewpoints of the equilibrium and kinetics of the pyrolysis reaction (it is necessary to have a final temperature in excess of 800° C. for satisfactory per pass conversion of the added ethane). A full-scale process could therefore not achieve the performance given in Example 4 of Australian Patent Application 32442/89 without the addition of a substantial amount of extra heat into the pyrolysis zone. Thus, even with external preheating of ethane, an adiabatic fixed-bed reactor is not a practical option to obtain the reactor performance given in Example 4. The heat balance calculations also highlight the severe limitations of the concept disclosed in Australian Patent application 32,442/89 with respect to increasing the amount of ethane and higher hydrocarbons relative to the quantity of

TABLE 1

| Case | (Based on Example 4, p 22 of Australian Patent Application 32442/89) | |
|---|---|---|
| | Ethane Preheat Temp (°C.) | Final Temp after Pyrolysis (°C.) |
| 1 | 25 | 641 |
| 2 | 300 | 665 |
| 3 | 600 | 702 |

(b) The Present Process

Heat balance calculations have been conducted for a fluid bed reactor operating at 850° C. under the conditions given in the Example of the present invention given herein. Note that the ethane converted per mol of methane converted in oxidative coupling (i.e. 0.668 mol/mol) is almost double that given in the examples in Australian Patent Application 32,442/89.

The calculations show that it is only necessary to preheat the added ethane to 570° C. and the methane/oxygen feed to 580° C. (both these operations being easily attainable with conventional engineering practice) to provide a heat-balanced, adiabatic fluidised-bed in which the required degree of methane oxidative coupling and ethane pyrolysis are achieved under essentially isothermal conditions at 850° C.

However if, for whatever reason, less external preheat of the feed gases is desirable (or if extra ethane is available for pyrolysis), the extra heat required by the reactor can be generated in situ simply by operating the methane oxidative coupling section of the fluidized-bed in a more highly exothermic manner (i.e. at a higher per pass methane conversion and a lower selectivity to hydrocarbons). In practice this can be achieved simply by adjusting the oxygen to methane ratio of the feed gas to the oxidative coupling reaction.

The fluidised-bed reactor has great flexibility with respect to the composition of the feedstock for the combined coupling/pyrolysis process as well as providing the energy required for the downstream sections of the process.

We claim:

1. A process for the production of ethylene and other olefinically unsaturated hydrocarbons from a first methane rich gas stream and a second gas stream rich in ethane and/or other higher hydrocarbons, comprising:
   (a) introducing the first gas stream together with molecular oxygen into a lower zone of a fluidised-bed of particles which are catalytically active in promoting an exothermic oxidative coupling reaction to produce ethylene and other hydrocarbons,
   (b) mixing the second gas stream into the fluidised-bed above the level at which essentially all of the molecular oxygen has been consumed, and
   (c) subjecting the mixture resulting from step (b) to an endothermic pyrolysis reaction in an upper zone of the fluidised-bed to produce further ethylene and other olefinically unsaturated hydrocarbons, the process is characterized in that the endothermic pyrolysis step (c) is carried out without the addition of heat to the reactor other than the heat content of the first and second gas streams and the heat generated by the exothermic oxidative coupling reaction.

2. A process as claimed in claim 1 in which the operation of the fluidised-bed causes the circulation of the particles in such a manner that there is an efficient transfer of the exothermic heat from the oxidative coupling zone to the pyrolysis zone so that the reactions of steps (a) and (c) are carried out at average temperatures within 100° C. of one another.

3. A process as claimed in claim 2 in which the oxidative coupling reaction of step (a) and the pyrolysis reaction of step (c) are conducted at temperatures which are each between 770° and 930° C. and are within 50° C. of one another.

4. A process as claimed in claim 1 in which the particles of the fluidised-bed are recirculated within a single reaction vessel.

5. A process as claimed in claim 1 in which catalyst recirculation is external to a reactor vessel or vessels containing the fluidised-bed.

6. A process as claimed in claim 1 in which the mol ratio of ethane or higher hydrocarbons converted by pyrolysis of the second stream t that of methane converted by oxidative coupling of the first stream is in the range of from 0.4:1 to 3:1.

7. A process as claimed in claim 1 in which the conditions of methane conversion and hydrocarbon selectivity in the oxidative coupling reaction are adjusted such that the amount of energy recoverable therefrom is just equal to that required to sustain the pyrolysis reaction.

8. A process as claimed in claim 1 in which hydrogen produced by the process is utilized outside the fluidized-bed to convert at least part of the carbon oxides generated by the oxidative coupling reaction back to methane which is then recycled into the fluidised-bed.

9. A process as claimed in claim 1 in which the process is based on natural gas as a feed stock and in which the process includes a gas pretreatment step which separates at least part of the non-methane hydrocarbons from the methane present in the natural gas to form the second gas stream.

* * * * *